US012295568B2

(12) United States Patent
Winslow (10) Patent No.: US 12,295,568 B2
(45) Date of Patent: May 13, 2025

(54) ADJUSTABLE LOOP SUTURE CONSTRUCT FOR JOINT REPAIR (71) Applicant: Biomet Manufacturing, LLC, Warsaw, IN (US)

(72) Inventor: Nathan A. Winslow, Scottsdale, AZ (US)

(73) Assignee: Biomet Manufacturing, LLC, Warsaw, IN (US)

( * ) Notice: Subject to any disclaimer, the term of this patent is extended or adjusted under 35 U.S.C. 154(b) by 386 days.

(21) Appl. No.: 17/880,206

(22) Filed: Aug. 3, 2022

(65) Prior Publication Data

US 2023/0088038 A1 Mar. 23, 2023

Related U.S. Application Data (60) Provisional application No. 63/315,652, filed on Mar. 2, 2022, provisional application No. 63/245,529, filed on Sep. 17, 2021.

(51) Int. Cl.
*A61B 17/06* (2006.01)
*A61B 17/00* (2006.01)
*A61B 17/04* (2006.01)

(52) U.S. Cl.
CPC .... *A61B 17/06166* (2013.01); *A61B 17/0401* (2013.01); *A61B 2017/00867* (2013.01)

(58) Field of Classification Search
CPC ............ A61B 17/0401; A61B 17/0482; A61B 17/0485; A61B 17/06166; A61B 2017/00867; A61B 2017/06042; A61B 2017/0608; A61B 2017/06095; A61B 2017/061; A61B 2017/06185; A61B 2017/0496; A61B 2017/0495; A61B 2017/0498; A61B 2017/06009; A61B 2017/06052; A61B 2017/06004
USPC .......................................................... 606/144
See application file for complete search history.

(56) References Cited

U.S. PATENT DOCUMENTS

| | | | |
|---|---|---|---|
| 2009/0082805 A1* | 3/2009 | Kaiser .............. | A61B 17/06166 606/228 |
| 2010/0198235 A1* | 8/2010 | Pierce ................ | A61B 17/0469 606/148 |
| 2011/0245850 A1* | 10/2011 | van der Burg ......... | A61B 90/39 606/145 |
| 2015/0250476 A1* | 9/2015 | Feezor ................ | A61B 17/064 606/228 |

* cited by examiner

*Primary Examiner* — Jocelin C Tanner
(74) *Attorney, Agent, or Firm* — Schwegman Lundberg & Woessner, P.A.

(57) ABSTRACT

Disclosed herein are suture systems and method of use thereof. The suture systems can include a passer, a needle, a first suture, and a second suture. The needle can be sized to pass through a cavity defined by the passer and define an attachment member. The first suture can include a first end, a second end, and a portion sized to be received by the attachment member and pass through the passer. The second suture can include a suture passage extending from a suture inlet to a suture exit. The first suture can be operable to pull a portion of the second suture at least partially around an anatomical structure. The second suture can be operable to reduce an anatomical structure when a first end of the second suture is passed through the suture passage.

14 Claims, 6 Drawing Sheets

ADJUSTABLE LOOP SUTURE CONSTRUCT FOR JOINT REPAIR

PRIORITY CLAIM

The present application claims priority to U.S. Provisional Application No. 63/245,529, entitled "Adjustable Loop Suture Constructs for Joint Repair," filed on Sep. 17, 2021 and claims priority to U.S. Provisional Application No. 63/315,652, entitled "Adjustable Loop Suture Construct for Joint Repair," filed on Mar. 2, 2022; the contents of each of which are hereby incorporated by reference in their entirety.

FIELD OF THE DISCLOSURE

The present disclosure generally relates to surgical sutures and methods of use thereof. More specifically, the present disclosure relates to suture systems including passers, needles, a plurality of sutures, and methods of use thereof.

BACKGROUND

The successful reattachment of soft tissue to bone can be a significant concern, especially in the sports medicine industry. The majority of soft tissue repairs involve the use of sutures. In such methods, an anchor or tack is readied for insertion into bone and a suture is passed through and/or around tissue and the anchor or tack and knotted or otherwise connected thereto. While holding tension on the suture, joint stability is evaluated and the anchor or tack is deployed into the bone, finalizing the repair.

SUMMARY

The following, non-limiting examples, detail certain aspects of the present subject matter to solve the challenges and provide the benefits discussed herein, among others.

Example 1 is a suture system comprising: a passer that defines a first passer opening, a second passer opening, and a passer cavity extending from the first passer opening to the second passer opening; a needle sized to pass into the first passer opening, through the passer cavity, and out the second passer opening, the needle defining an attachment member; a first suture including a first end and a second end, at least a portion of the first suture sized to be received by the attachment member and pass through the passer cavity; and a second suture including a first end, the second suture defining a suture inlet, a suture exit, and a suture passage extending from the suture inlet to the suture exit, wherein the first suture is operable to pull a portion of the second suture at least partially around an anatomical structure, wherein the second suture is operable to reduce the anatomical structure when the first end of the second suture is passed through the suture inlet, the suture passage, and the suture exit.

In Example 2, the subject matter of Example 1 optionally includes wherein the second suture is a braided suture.

In Example 3, the subject matter of any one or more of Examples 1-2 optionally include wherein the first end of the second suture passing through the suture inlet, the suture passage, and the suture exit forms a constriction construct.

In Example 4, the subject matter of any one or more of Examples 1-3 optionally include wherein a portion of the passer proximate the second passer opening is curved.

In Example 5, the subject matter of any one or more of Examples 1-4 optionally include wherein a portion of the passer proximate the second passer opening forms an arc including a chord extending at least 180°.

In Example 6, the subject matter of any one or more of Examples 1-5 optionally include wherein the needle is made of a shape memory alloy.

In Example 7, the subject matter of any one or more of Examples 1-6 optionally include wherein the attachment member is an aperture.

In Example 8, the subject matter of any one or more of Examples 1-7 optionally include wherein the attachment member is a notch.

In Example 9, the subject matter of any one or more of Examples 1-8 optionally include wherein the passer is one of a plurality of passers, each of the plurality of passers including a different profile.

In Example 10, the subject matter of any one or more of Examples 1-9 optionally include wherein the needle is one of a plurality of needles, each of the plurality of needles including a different stiffness or radius of curvature.

Example 11 is a suture system comprising: a passer that defines a first passer opening, a second passer opening, and a passer cavity extending from the first passer opening to the second passer opening; a needle sized to pass into the first passer opening, through the passer cavity, and out the second passer opening, the needle defining a notch; a first suture including a first end and a second end, at least a portion of the first suture sized to be received by the notch and pass through the passer cavity; and a second suture including a first end, the second suture defining a suture inlet, a suture exit, and a suture passage extending from the suture inlet to the suture exit, the second suture being a braided suture, wherein the first suture is operable to pull a portion of the second suture at least partially around an anatomical structure, wherein the second suture is operable to reduce the anatomical structure when the first end of the second suture is passed through the suture inlet, the suture passage, and the suture exit via a constriction constructed formed by the first end of the second suture passing through the suture inlet, the suture passage, and the suture exit.

In Example 12, the subject matter of Example 11 optionally includes wherein a portion of the passer proximate the second passer opening is curved.

In Example 13, the subject matter of any one or more of Examples 11-12 optionally include wherein a portion of the passer proximate the second passer opening forms an arc including a chord extending at least 180°.

In Example 14, the subject matter of any one or more of Examples 11-13 optionally include wherein the needle is made of a shape memory alloy.

In Example 15, the subject matter of any one or more of Examples 11-14 optionally include wherein the passer is one of a plurality of passers, each of the plurality of passers including a different profile.

In Example 16, the subject matter of any one or more of Examples 11-15 optionally include wherein the needle is one of a plurality of needles, each of the plurality of needles including a different stiffness or radius of curvature.

Example 17 is a method for reducing an anatomical structure, the method comprising: passing a portion of a passer at least partially around a portion of the anatomical structure, the passer defining a cavity; passing a needle through the cavity of the passer to expose a notch of the needle proximate the anatomical structure; securing a first suture to the notch of the needle; pulling the needle through the cavity thereby pulling a portion of the first suture through the passer; securing a second suture to the first suture; pulling a portion of the second suture around the anatomical structure using the first suture; reducing the anatomical structure using the second suture; and forming a constriction construct using the second suture to secure the anatomical structure.

In Example 18, the subject matter of Example 17 optionally includes wherein the second suture is a braided suture, and forming the constriction construct includes passing a first end of the second suture through a suture passage defined by the second suture.

In Example 19, the subject matter of any one or more of Examples 17-18 optionally include wherein reducing the anatomical structure includes creating tension on a first end and a second end of the second suture thereby causing a first portion of the anatomical structure to move into proximity of a second portion of the anatomical structure.

In Example 20, the subject matter of any one or more of Examples 17-19 optionally include wherein reducing the anatomical structure and forming the constriction construct occur simultaneously.

In Example 21, the sutures, suture systems, and/or methods of any one or any combination of Examples 1-20 can optionally be configured such that all elements or options recited are available to use or select from.

BRIEF DESCRIPTION OF THE FIGURES

In the drawings, which are not necessarily drawn to scale, like numerals can describe similar components in different views. Like numerals having different letter suffixes can represent different instances of similar components. The drawings generally illustrate, by way of example, but not by way of limitation, various embodiments discussed in the present document.

Corresponding reference characters indicate corresponding parts throughout the several views. The examples set out herein illustrate example embodiments of the disclosure, and such examples are not to be construed as limiting the scope of the disclosure in any manner.

DETAILED DESCRIPTION

During surgical procedures, bone, tissue, or other anatomical structures can interfere with a surgeon's ability to place sutures. The sutures can be used to reduce and/or otherwise set anatomical structures to repair damage to the anatomical structures. For example, the sutures can be used to reduce a joint to allow tendons and/or ligaments that may have been torn, severed, and/or otherwise injured to allow a surgeon to suture the tendons and/or ligaments.

As disclosed herein, a suture system can be used to help the surgeon position the sutures. The suture system can include a passer that can include a body that defines a first passer opening, a second passer opening, and a passer cavity extending from the first passer opening to the second passer opening. A needle can be sized to pass into the first passer opening, through the passer cavity, and out the second passer opening. The needle can define an attachment member.

A first suture can include a first end and a second end. A portion of the first suture can be sized to be received by the attachment member and pass through the passer cavity. A second suture can include a first end. The second suture can define a suture inlet, a suture exit, and a suture passage extending from the suture inlet to the suture exit. The first suture can be operable to pull a portion of the second suture at least partially around an anatomical structure, such as bone, ligaments, tendons, etc. The second suture can be operable to reduce the anatomical structure when the first end of the second suture is passed through the suture inlet, the suture passage, and the suture exit. The suture passage can form a constriction construct that secures tension in the second suture and holds the anatomical structure in a reduced state.

The above discussion is intended to provide an overview of subject matter of the present patent application. It is not intended to provide an exclusive or exhaustive explanation of the disclosure. The description below is included to provide further information about the embodiments of the present patent application.

Figure 1A:
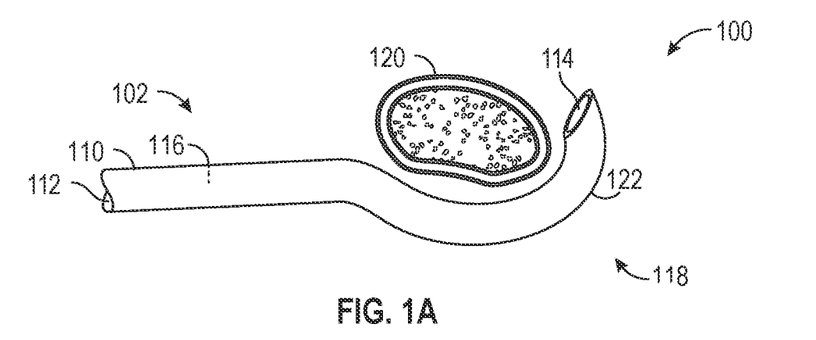
FIGS. 1A, 1B, and 1C illustrate a suture system in accordance with at least one example of this disclosure.
Figure 1B:
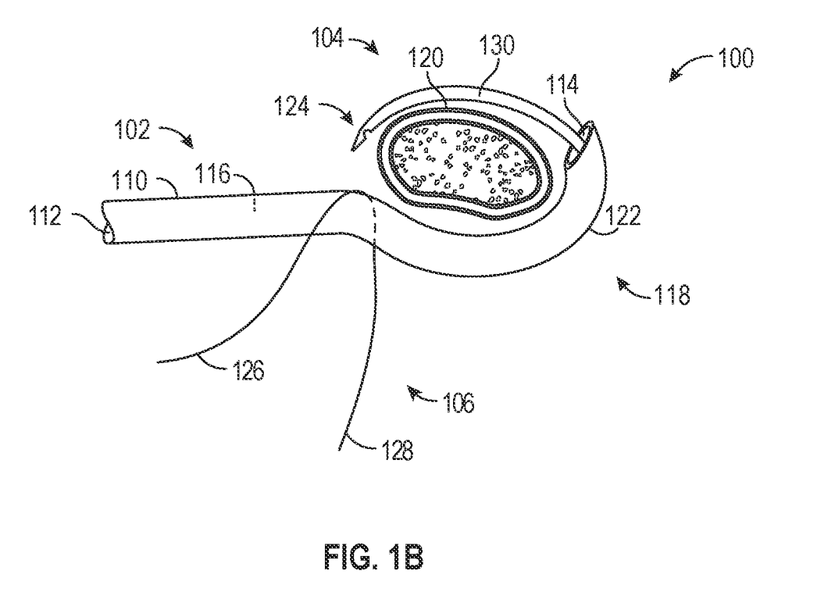
Figure 1C:
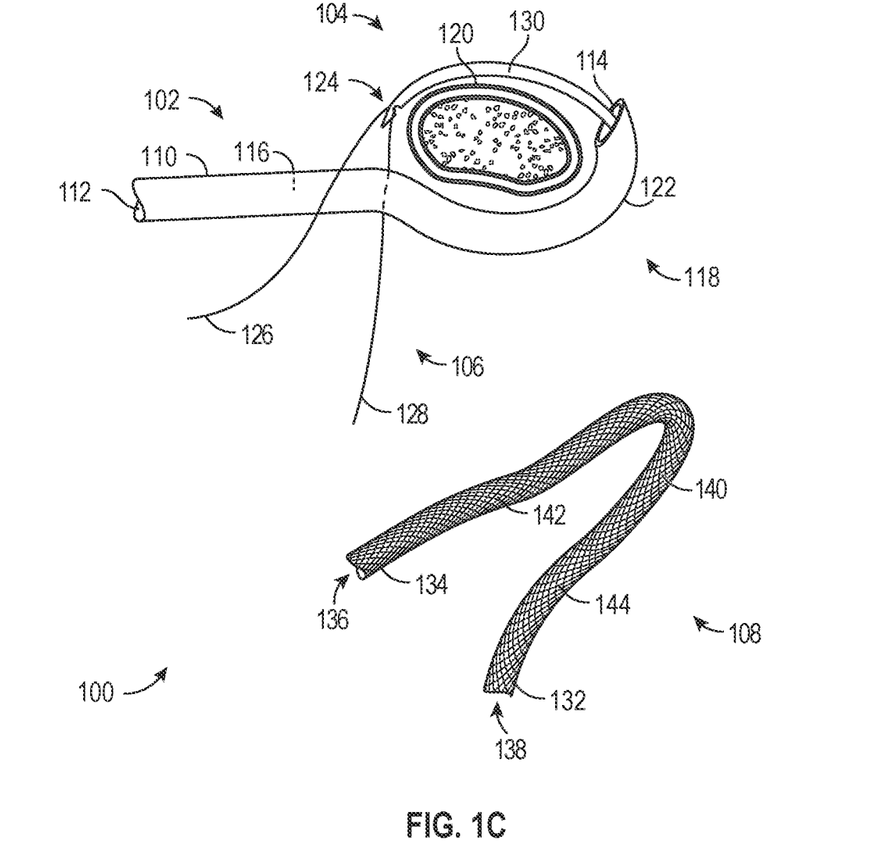

Turning now to the figures, FIGS. 1A, 1B, and 1C illustrate a suture system 100 in accordance with at least one example of this disclosure. Suture system 100 can include a passer 102, a needle 104, a first suture 106, and a second suture 108. Passer 102 can include a body 110 that defines a first passer opening 112, a second passer opening 114, and a passer cavity 116 that can extend from first passer opening 112 to the second passer opening 114.

As disclosed herein, passer 102 can include a portion 118 that is curved. For example, portion 118 of passer 102 can be located proximate second passer opening 114. Portion 118 can allow passer 102 to guide needle 104 around anatomical structures, such as anatomy 120, as disclosed herein. For instance, portion 118 of passer 102 can be curved to form an arc that can include a chord 122. Chord 122 formed by the portion 116 can extend at least 90°, 180°, and 270°. The curvature of portion 116 can allow passer 102 to extend at least partially around anatomy 120.

Passer 102 can be constructed of metals, polymers, ceramics, and/or any combinations thereof. Passer 102 can be constructed by bending a section of tubing, either square or round tubing, to form the curved in portion 118. Passer 102 can be printed using three-dimensional printers, extruded, injection molded, etc. Passer 102 can be a disposable item that is for used with a single patient or an item that can be autoclaved for sterilization and used with multiple patients.

As disclosed herein, needle 104 can be sized to pass into first passer opening 112, through passer cavity 116, and out second passer opening 114. Needle 104 can define an attachment member 124. Attachment member 124 can include a notch for receiving first suture 106. For example, first suture 106 can include a first end 126 and a second end 128. As disclosed herein, at least a portion of first suture 106 can be sized to be received by attachment member 124 and pass through passer cavity 116. Still consistent with embodiments disclosed herein, attachment member 124 can include a hole or other aperture that first suture 106 can pass through, a protrusion that first suture 106 can be attached to, and/or a combination of features that enable first suture 106 to be attached to needle 104.

Needle 104 can be constructed of metals, polymers, ceramics, and/or any combinations thereof. For example, needle 104 can be constructed of a shape memory alloy that allows needle 104 to maintain a curved portion 130 after exiting passer 102. Needle 104 can be printed using three-dimensional printers, extruded, injection molded, etc. Needle 104 can be a disposable item that is for used with a single patient or an item that can be autoclaved for sterilization and used with multiple patients.

Second suture 108 can include a first end 132 and a second end 134. Second suture 108 can be a braided suture that defines a suture inlet 136, a suture exit 138, and a suture passage 140 extending from suture inlet 136 to suture exit 138. Suture inlet 136 and suture exit 138 can be formed by ends of second suture 108 as shown in FIG. 1C. Suture inlet 136 and suture exit 138 can also be apertures formed by the braiding of second suture 108 as indicated by reference numerals 142 and 144. Openings formed by the braiding of second suture can allow first end 132 and/or second end 134 to be passed into suture passage 140 to form a constriction construct for reducing or otherwise setting a joint or other anatomical structure as disclosed herein.

Figure 2A:
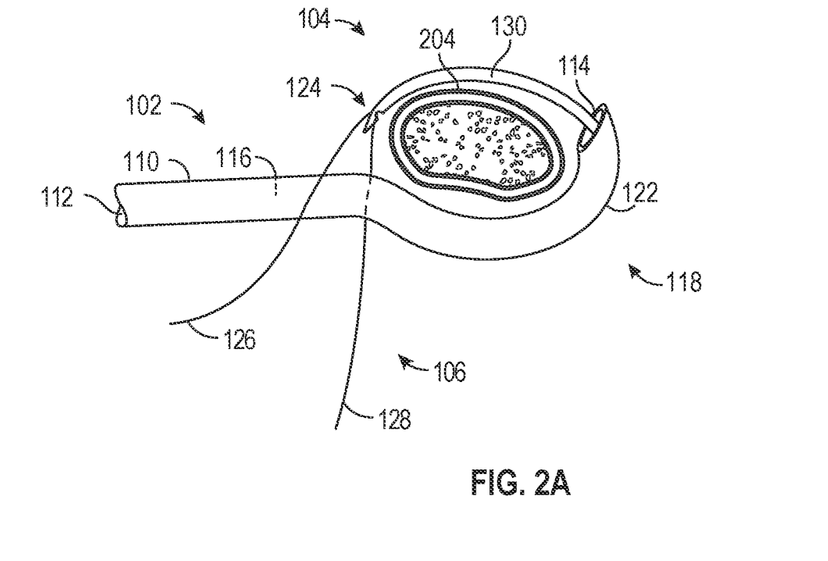
FIGS. 2A, 2B, 2C, 2D, 2E, 2F, 2G, and 2H a method in accordance with at least one example of this disclosure.
Figure 2B:
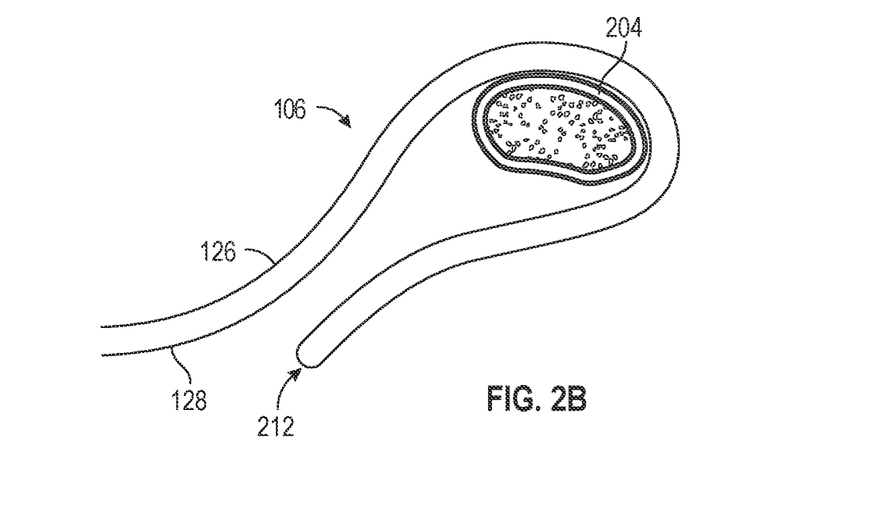

FIGS. 2A, 2B, 2C, 2D, 2E, 2F, 2G, and 2H illustrate a method for reducing an anatomical structure 202 comprising a first bone 204, a second bone 206, a first tendon portion 208, and a second tendon portion 210, in accordance with at least one example of this disclosure. As shown in FIG. 2A, needle 104 can be passed through passer 102, which can partially encircle first bone 204. Passing needle 104 through passer 102 can expose attachment member 124 proximate first bone 204. First suture 106 can be attached to needle 104 via attachment member 124. Needle 104 can then be retracted through passer 102 to pull first suture 106 around first bone 204 as shown in FIG. 2B.

Figure 2C:
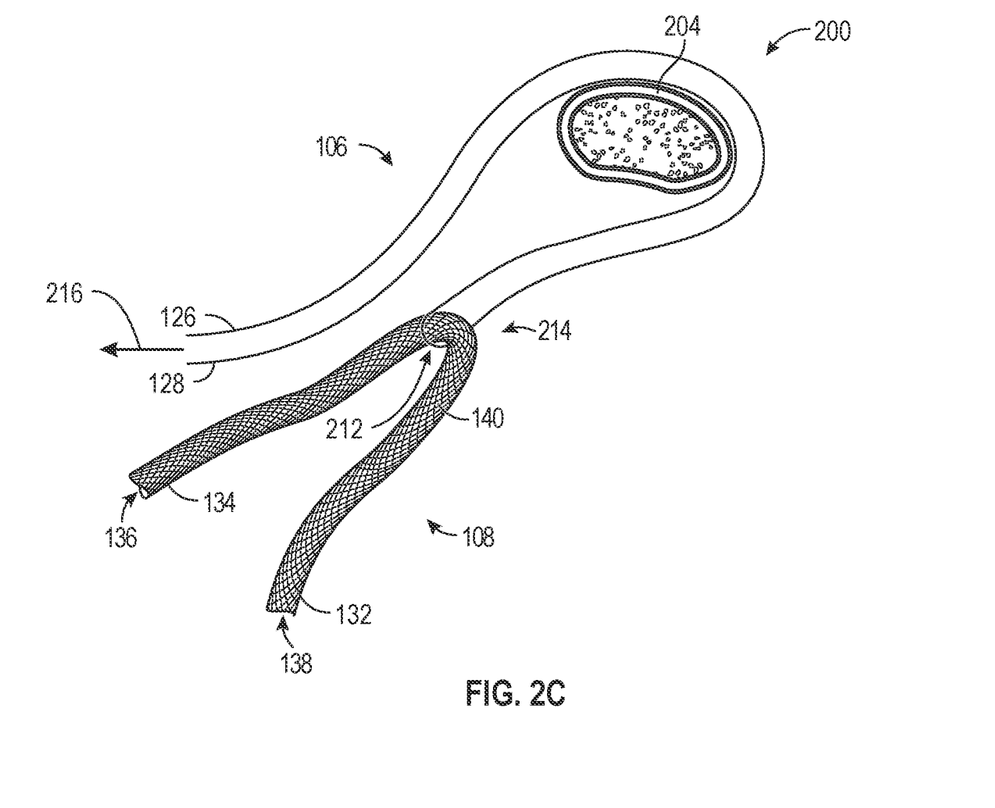
Figure 2D:
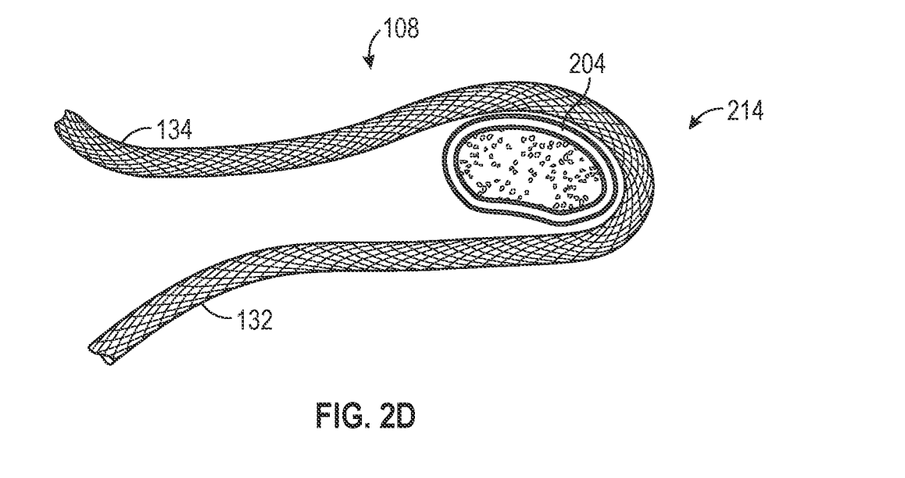
Figure 2E:
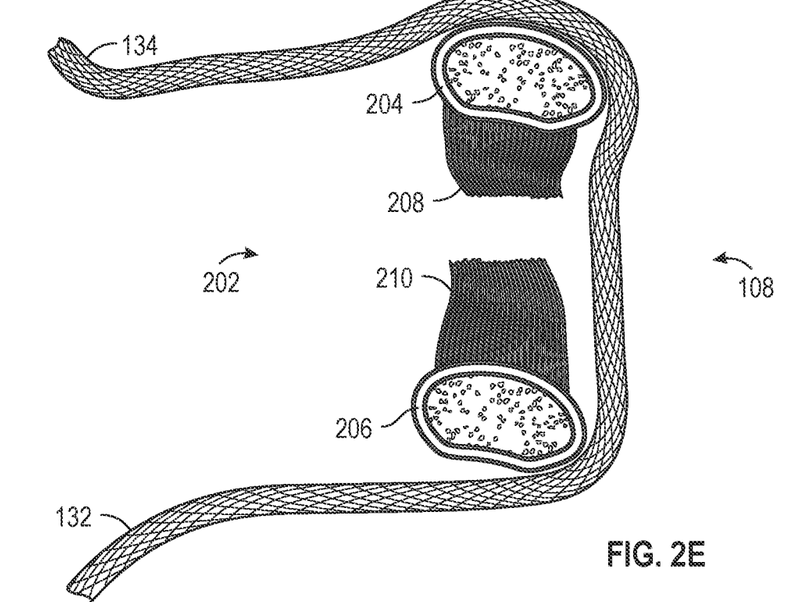

As shown in FIG. 2C, a portion 212 of first suture 106 can be wrapped around a portion 214 of second suture 108. Once second suture 108 is secured to first suture 106, first end 126 and second end 128 of first suture 106 can be pulled as indicated by arrow 216 to pull second suture 108 around first bone 204 as shown in FIG. 2D. The process can be repeated to pass second suture 108 around second bone 206 as shown in FIG. 2E.

Figure 2F:
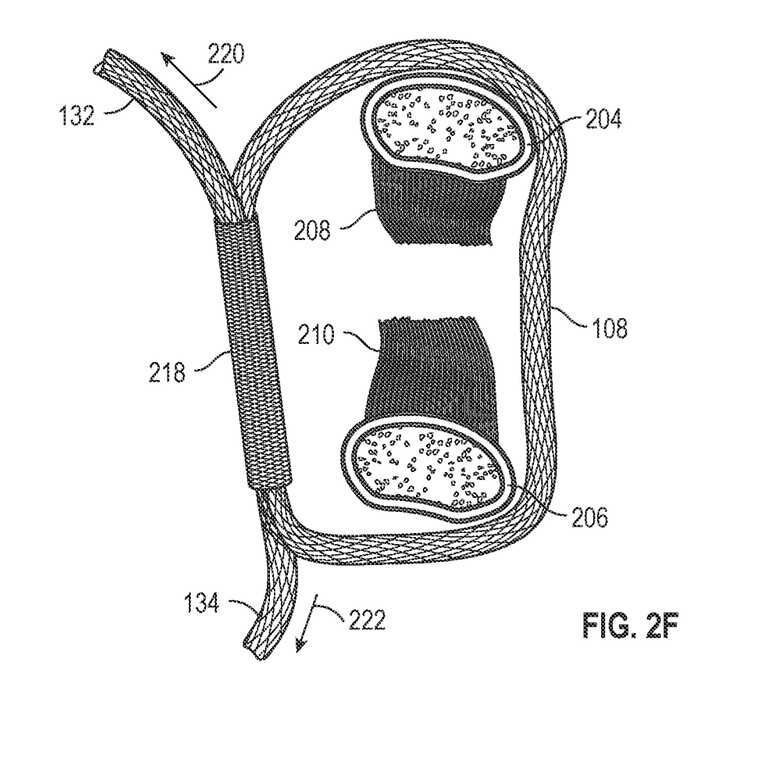

As shown in FIG. 2F, first end 132 and second end 134 of second suture 108 can pass through a constriction 218. Constriction 218 can be a portion of second suture 108. For example, when second suture 108 is a braided material first end 132 or second end 134 can be passed into a suture passage, such as suture passage 140, and exit in between strands of material that form the braided material.

Figure 2G:
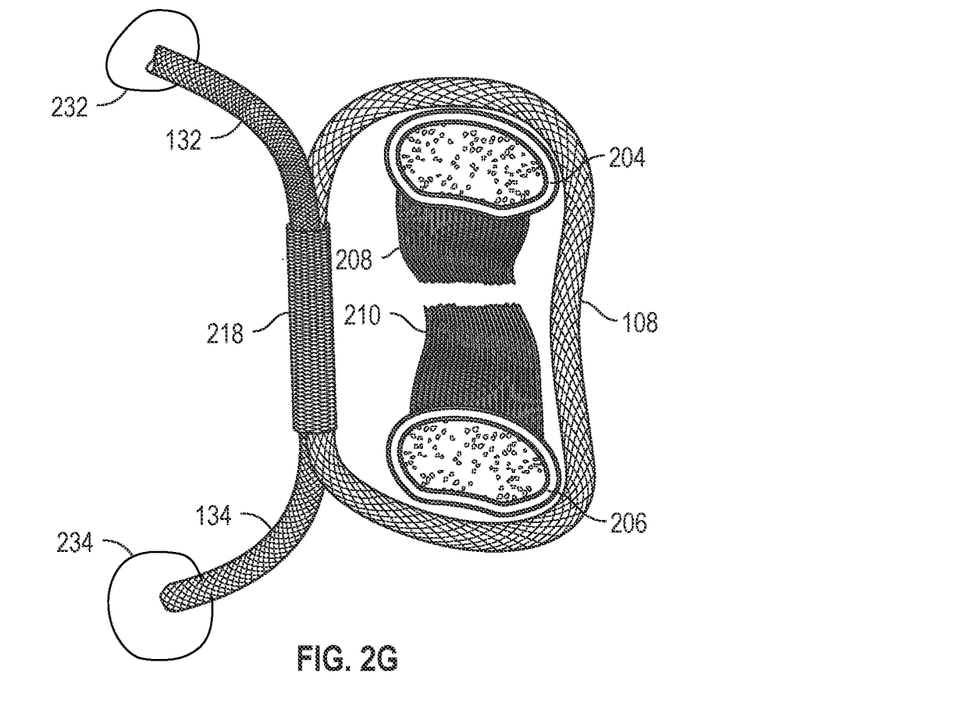

Pulling first end 132 and/or second end 134 as indicated by arrows 220 and 222 can cause second suture 108 to reduce first tendon portion 208 and second tendon portion 210 as shown in FIG. 2G. To assist with pulling the first end 132 and/or second end 134, a first loop 232 and a second loop 234 can be attached to first end 132 and second end 134, respectively. First and second loops 232 and 234 can be metal loops, that are passed through braided portions of second suture 108. First and second loops 232 and 234 can be made of a suture material, such as first suture 106. When first and second loops 232 and 234 are made of a suture material, a needle, such as needle 104 can be used to fish the suture material through first and second ends 132 and 134. After fishing the suture material through first and second ends 132 and 134, the surgeon can tie the suture material to form first and second loops 232 and 234 to a size convenient for his or her hands. Once anatomical structure 202 is set, the suture material that forms first and second loops 232 and 234 can be used to secure the constriction or removed depending on a preference of the surgeon, the procedure being performed, and/or the anatomical structure being repaired.

Still consistent with embodiments disclosed herein, constriction 218 can be a separate material. For example, constriction 218 can be a separate piece of braided material, such as the same material used to construct second suture 108. The material can form a passage similar to suture passage 140, in which first end 132 and second end 134 can pass.

Reducing anatomical structure 202 can also cause constriction 218 to form a constriction construct simultaneously.

Figure 2H:
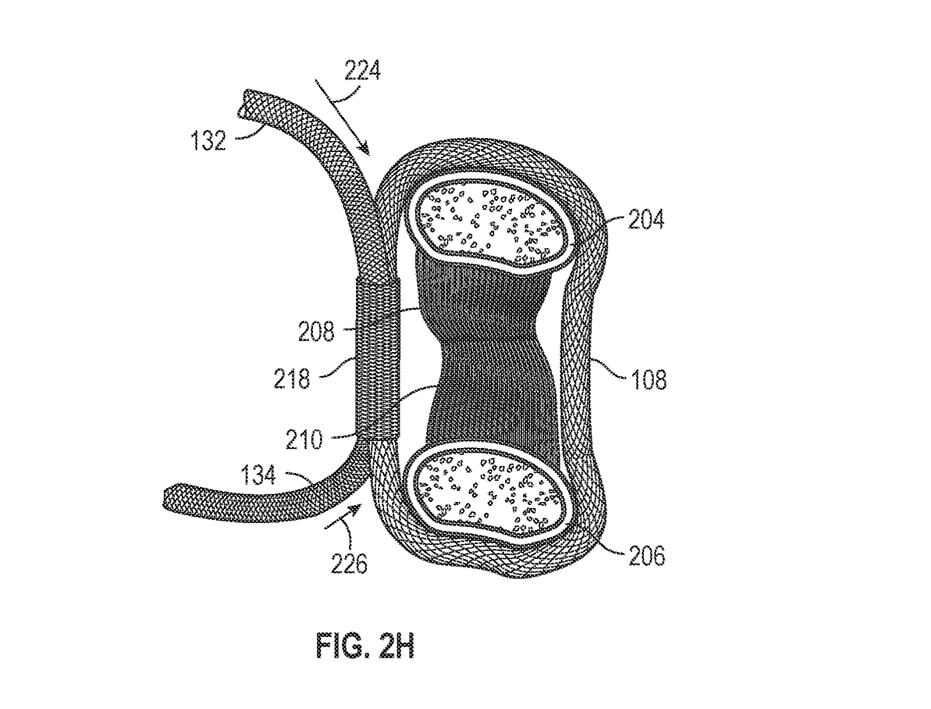

For example, tension within constriction 218 can prevent loosening of the reducing of anatomical structure 202. For example, as shown in FIG. 2H, anatomical structure 202 can be reduced to the point where first tendon portion 208 and second tendon portion 210 can be sutured together, such as with first suture 106, or a third suture. To allow the tendon to heal, constriction 218 can constrict first end 132 and second end 134 such that they are not able to move against forces as indicated by arrows 224 and 226.

As disclosed herein, passer 102 may be one of a plurality of passers. Each of the different passers can have different curvature profiles. For example, a first passer may have a curved portion that forms a 180° arc and a second passer may have a curved portion that forms a 235° arc. The different curved profiles can facilitate anatomical structures having different sizes and/or shapes. For example, the first passer may be used to pass first suture 104 around first bone 202 and the second passer may be used to pass first suture 104 around second bone 204.

In addition to differing curved portions, different passers in the plurality of passers may be different sizes. For example, needle 104 may be one of a plurality of needles that are made of wire having different gauges for each needle. The different passers in the plurality of passers may have different sizes to accommodate needles of different gauges. In addition, each of the needles may have a different stiffness and different passers may have different curvatures to accommodate the different stiffnesses. For example, the first passer may have a larger radius of curvature to accommodate a stiffer gauge needle and the second passer may have a smaller radius of curvature in which a needle with a lower stiffness can pass.

NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. § 1.72 (b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A method for reducing an anatomical structure, the method comprising:
   passing a portion of a passer at least partially around a portion of the anatomical structure, the passer defining a cavity;
   passing a needle through the cavity of the passer to expose a notch of the needle proximate the anatomical structure;
   securing a first suture to the notch of the needle;
   pulling the needle through the cavity thereby pulling a portion of the first suture through the passer;
   securing a second suture to the first suture;
   pulling a portion of the second suture around the anatomical structure using the first suture;
   reducing the anatomical structure using the second suture; and
   forming a constriction construct using the second suture to secure the anatomical structure.

2. The method of claim 1, wherein
   the second suture is a braided suture, and
   forming the constriction construct includes passing a first end of the second suture through a suture passage defined by the second suture.

3. The method of claim 1, wherein reducing the anatomical structure includes creating tension on a first end and a second end of the second suture thereby causing a first portion of the anatomical structure to move into proximity of a second portion of the anatomical structure.

4. The method of claim 1, wherein reducing the anatomical structure and forming the constriction construct occur simultaneously.

5. A method for reducing an anatomical structure, the method comprising:
   passing a portion of a passer at least partially around a portion of the anatomical structure, the passer defining a cavity;
   advancing a needle through the cavity, wherein said advancing leaves an attachment member of the needle exposed proximate the anatomical structure;
   securing a first suture to the attachment member of the needle;
   withdrawing the needle back through the cavity to thereby pull a portion of the first suture around the portion of the anatomical structure;
   securing a second suture to the first suture;
   pulling a portion of the second suture around the anatomical structure using the first suture;
   reducing the anatomical structure using the second suture; and
   forming a constriction construct using the second suture to secure the anatomical structure.

6. The method of claim 5, wherein said reducing the anatomical structure includes creating tension on a first end and a second end of the second suture thereby causing a first portion of the anatomical structure to move into proximity of a second portion of the anatomical structure.

7. The method of claim 5, wherein said reducing the anatomical structure and said forming the constriction construct occur simultaneously.

8. The method of claim 5, wherein the second suture is a braided suture.

9. The method of claim 5, wherein said forming the constriction construct includes passing a first end of the second suture through a suture passage defined by the second suture.

10. The method of claim 5, wherein said portion of the passer is curved.

11. The method of claim 5, wherein said portion of the passer forms an arc including a chord extending at least 180°.

12. The method of claim 5, wherein the needle is made of a shape memory alloy.

13. The method of claim 5, wherein the attachment member is an aperture.

14. The method of claim 5, wherein the attachment member is a notch.

* * * * *